United States Patent [19]

Shull et al.

[11] 4,172,140

[45] Oct. 23, 1979

[54] ANTIMICROBIAL HYDANTOIN DERIVATIVE COMPOSITIONS AND METHOD OF USE

[75] Inventors: Samuel E. Shull, Cogan Station, Pa.; Edward O. Bennett, Houston, Tex.

[73] Assignee: Glyco Chemicals, Inc., Greenwich, Conn.

[21] Appl. No.: 826,265

[22] Filed: Aug. 19, 1977

[51] Int. Cl.$^2$ .................. A01N 9/22; A01N 9/24; A01N 9/02
[52] U.S. Cl. .................. 424/273 R; 424/317; 424/334; 252/51.5 A
[58] Field of Search .................. 424/273, 334, 317; 252/51.5

[56] References Cited

U.S. PATENT DOCUMENTS 3,987,184  10/1976  Foelsch .................. 424/273

OTHER PUBLICATIONS

Chemical Abstracts, vol. 85 (1976), p. 187144v.
Chemical Abstracts, vol. 63 (1965), p. 6042h.

*Primary Examiner*—V. D. Turner
*Attorney, Agent, or Firm*—Cushman, Darby & Cushman

[57] ABSTRACT

Antimicrobial compositions for inhibiting the growth of microorganisms in an aqueous fluid medium comprising an admixture of a condensation product of 5,5-dimethylhydantoin and formaldehyde with a chelating agent. A method for inhibiting microorganism growth in aqueous fluid media, particularly such media containing fatty oil or petroleum base components and modified metal working fluids also described.

10 Claims, No Drawings

ANTIMICROBIAL HYDANTOIN DERIVATIVE COMPOSITIONS AND METHOD OF USE

BACKGROUND OF THE INVENTION

Antimicrobial compositions are generally added to various kinds of aqueous fluid media to reduce or inhibit the growth of microorganisms.

For instance, a wide variety of industrial aqueous fluid media are known such as metal working fluids used with metal working equipment.

The development of high speed metal cutting and grinding has resulted in the creation of lubricants containing oils and chemicals stabilized in water. These fluids impart the cooling qualities of water and the lubricating properties of oil which prolongs the life of cutting tools, reduces heat production, improves surface finish of the metal being machined, prevents warping and leaves a rust-inhibiting film of oil on the worked piece.

Normally these fluids consist of fatty or petroleum oils, soaps, or synthetic based materials and additional additives such as antifoam agents, EP additives, preservatives, coupling agents and rust inhibitors. The coolants are generally marketed in the form of concentrates which are normally diluted with water by the user in ratios of 1 part oil to about 20-40 parts of water, but these ratios may vary with particular operations. The lubricant is supplied to a machine from either an individual tank containing fifty to one hundred gallons or from a large sump containing thousands of gallons which supplies many machines.

One of the problems often associated with such aqueous fluid media arises from the susceptibility of the media to the infestation and growth of various microorganisms such as bacteria and fungi (which particularly feed on the organic components thereof). The presence and buildup of such microorganisms can often lead to interference in the metal working operations as a result of the clogging of filters, build up of slime and sludge, development of odors, rust, emulsion instability, reduced tool life and poor finish. Furthermore, in machine shops where the workers' hands necessarily come in contact with the cutting oil, usually containing finely divided sharp metal cuttings, serious problems of dermatitis may arise. These and other such similar problems have resulted in the continuing need for better antimicrobial additives for aqueous fluid media such as metal working fluids. Much effort has been devoted in recent years to controlling this problem; however, it continues to be a major annoyance which costs the metal working industry many millions of dollars each year.

A number of suggestions have been made for inhibiting the growth of bacteria in aqueous fluids such as those described in U.S. Pat. Nos. 4,012,261; 3,591,679; 3,408,843 and 3,240,701. The use of various formaldehyde preservatives for metal working fluids including monomethylol dimethyl hydantoin and dimethylol dimethyl hydantoin has also been proposed (See Bennett, E. O., *Int. Biodetn. Bull.* 9 pages 95-100, 1973 and Maeda et al., *Agr. Biol. Chem.*, 40, 1111-2222, 1976).

Gray and Wilkinson in *J. Gen. Microbiol.*, 39, 385-399 (1965) and *J. App. Bact.*, 28, 153-164 (1965) describe the action of the ethylenediaminetetraacetic acid (hereinafter sometimes referred to as "EDTA") on some bacteria. The effectiveness of such chelating agents as EDTA alone for bacterial control in aqueous systems is disputed as evidenced by U.S. Pat. Nos. 3,240,701; 3,408,843 and 3,591,679. The antimicrobial compositions used in metal working fluids seem to suffer from one or more disadvantages including high-cost, unacceptable toxicity or low degree of effectiveness at the present state of the art.

Accordingly, it is the primary object of the present invention to provide an effective antimicrobial composition formulation for use in an aqueous fluid medium.

A further object of the present invention is to provide an effective relatively non-toxic method for inhibiting the growth of microorganisms in an aqueous fluid medium susceptible to such growth.

These and other objects of our invention will be apparent from the discussion which follows.

SUMMARY OF THE INVENTION

We have discovered antimicrobial compositions, suitable for inhibiting the growth of microorganisms in an aqueous fluid medium susceptible to such growth, comprising as an active ingredient a condensation product of 5,5-dimethyl hydantoin and formaldehyde (e.g., the mono- or dimethylol dimethyl hydantoin) in combination with a water-soluble chelating agent. A preferred antimicrobial composition formulation comprises as an active ingredient 1,3-dimethylol-5,5-dimethylhydantoin (hereinafter sometimes referred to as "DMDMH") in combination with ethylenediaminetetraacetic acid or a water-soluble salt thereof, e.g. with alkali metals or ammonium salts.

These antimicrobial compositions when added to an aqueous fluid medium provide an unexpected degree of preservation and antimicrobial activity over what one would expect from results obtained by using the hydantoin-formaldehyde condensation product or chelating agent (i.e., DMDMH, EDTA, or a salt thereof) alone.

DETAILED DESCRIPTION OF THE INVENTION

The antimicrobial compositions of our invention thus comprise an active combination of a condensation product of 5,5-dimethyl hydantoin and formaldehyde (e.g., 1,3-dimethylol-5,5-dimethyl hydantoin, 1-methylol-5,5-dimethyl hydantoin, or 3-methylol-5,5-dimethyl hydantoin, 1,3-dimethyloloxymethylene-5,5-dimethyl hydantoin and mixtures thereof) and a water-soluble chelating agent.

Condensation products of 5,5-dimethylhydantoin (hereinafter referred to as "DMH") and formaldehyde are well known. For example, DMDMH may be prepared as described in U.S. Pat. No. 3,987,184, the entire contents of which are incorporated herein by reference. This patent describes the use of e.g., 40-75% aqueous solutions of DMDMH as a formaldehyde donor, as well as a preservative, in various pastes, soaps, skin creams, liquid shampoos and other similar preparations.

The condensation products of DMH and formaldehyde as used herein are intended to include those products wherein 1,2 or more moles of formaldehyde are condensed with each mole of DMH. Thus, the condensation products include those wherein more than 2 moles of formaldehyde may be condensed with each mole of DMH, such as, for example 1-methylol-3-methyloloxymethylene-5,5-dimethyl hydantoin and 1,3-dimethyloloxymethylene-5,5-dimethyl hydantoin.

When added to an aqueous fluid medium, we have now found that when an antimicrobial DMH-formaldehyde condensation product such as DMDMH is used in combination with a chelating agent such as EDTA or a water-soluble EDTA salt a greatly enhanced degree of antimicrobial activity is obtained. When a chelating agent such as EDTA (or an EDTA water-soluble salt) is used alone (at the concentration levels here involved), there is generally no significant antimicrobial activity exhibited. Further, while antimicrobial activity is observed when the DMH-formaldehyde condensation product alone is used by itself, the level of such activity is less than is desired. However, when according to the invention the chelating agent is used in combination with the DMH-formaldehyde condensation product, for reasons not entirely clear at present, the presence of the chelating agent has an unexpected effect of potentiating or greatly enhancing the antimicrobial activity of the said hydantoin-condensation component, as is more fully described below.

As used herein, chelating agents are defined as water-soluble substances which when added to an aqueous fluid medium, reduce the normal ionic effects of the cations present. Suitable chelating agents according to the present invention may include EDTA, and diethylenetriamine pentaacetic acid (hereinafter sometimes DTPA) and similar compounds as well as their water-soluble salts (e.g., sodium salts).

While ethylenediaminetetraacetic acid itself may be employed, it is preferred to use one of its water-soluble salts, such as alkali metal salts, for example the disodium salt (sometimes referred to as "EDTA diNa") or the tetrasodium salt (sometimes referred to hereinafter as "EDTA-tNa"). The comparable potassium salts, and the ammonium salts may also be used.

The antimicrobial compositions of the present invention may thus generally be formulated to contain the active hydantoin-formaldehyde condensation product and chelating agent in a weight ratio ranging from about 0.25:1 to 20:1, and preferably about 1:1 to 5:1 hydantoin to chelating agent with or without additional inert liquid vehicles or dispersants, or solid extenders, or inert carriers. Most preferably, and conveniently, compositions may be formulated containing less than about 5% by weight of the chelating agent.

In use these antimicrobial composition formulations may be added to an aqueous fluid medium in the form of a solid block or tablet, as a powder, or preferably as a solution.

In order to achieve practical level of inhibition of microorganism growth in the aqueous fluid medium it is necessary to include therein the combination of active hydantoin (i.e., mono- or dimethylol-5,5-dimethyl hydantoin) and chelating agent in an amount sufficient to inhibit the growth of microorganisms. As used herein, the term inhibitive amount is to be understood as that amount of the said combination which when added to an aqueous fluid medium will acceptably inhibit the growth of microorganisms in the use of said medium. Furthermore, this level of inhibition will be greater than the additive level of inhibition one would obtain with the active hydantoin product in the absence of the chelating agent (e.g., 1 part DMDMH and 1 part EDTA is more inhibitory than 2 parts DMDMH alone).

Generally at least 500 parts of the chelating agent and at least 500 parts of active hydantoin are added per million parts of the aqueous fluid medium. Thus, the chelating agent may be added in amounts ranging from about 500 to 4000 parts per million (ppm) of the aqueous fluid medium. Likewise, one may suitably add from about 500 to 10,000 parts of active hydantoin per million parts of the aqueous fluid medium. The weight ratio of condensation product and chelating agent may range suitably from about 0.25:1 to 20:1 and preferably about 1:1 to 5:1. Of course, with an increase in water hardness, the proportional amount of chelating agent may need to be increased to achieve desired results.

As used herein, the term aqueous fluid medium is meant to encompass water, oil in water, water in oil emulsions (including concentrates) and like compositions susceptible to the infestation and growth of microorganisms. Thus, for instance, metal working fluids or cutting oil fluids (in diluted as well as undiluted form) together with conventional additives such as corrosion inhibitors etc. are to be included.

The antimicrobial compositions may be added directly to undiluted metal working fluids. As used herein the term "metal working fluid" is intended to encompass those compositions known in the art as "metal cutting fluids", "cutting fluids", "coolants", "lubricants" "rolling oils", "drawing fluids", "mold release fluids", "grinding fluids" and like products used in the processing of metals as described more fully by Springborn, R. K. "Cutting and Grinding Fluids:" Selection and Application, ASTME (1967) and Wilbert J. Olds, "Lubricants, Cutting Fluids and Coolants", Cahner's Books, the entire contents of each being incorporated herein by reference. Emulsifiable or water miscible oils are widely used in the industry. Mixed with water, they form emulsions for use in rolling, drawing, machining and grinding where the need is for both cooling and lubrication. More recently, water miscible fluids using less oil (or no oils) and based on chemicals with or without surface active agents, have provided industry with products of even greater heat conducting properties for still higher machining rates.

The following examples are offered in order to more fully illustrate the invention, but are not to be construed as limiting the scope thereof.

EXPERIMENTAL PROCEDURE

Test units employed consisted of quart jars placed in rows. Above each row a metal framework was constructed to support the aeration system which consisted of aquarium valves connected together with plastic tubing. The amount of aeration of each jar unit was controlled by adjusting the valves. Capillary pipettes were employed as aerators to produce a fine stream of bubbles.

Five hundred ml of tap water (moderate hardness) was added to each jar unit. DMDMH and EDTA and DTPA were used as obtained from the manufacturer and the desired amount (wt/vol or vol/vol) of each product was added to each unit along with the required amount of coolant concentrate to produce the desired oil-water ratio. (DMDMH was used as a 55% aqueous solution, identified as "DMDMH-55"). The unit was then made up to a total volume of 600 ml with additional tap water.

The jars were inoculated with a mixture of bacteria and fungi which were obtained and maintained as described in "The Deterioration of Metal Cutting Fluids," Prog. Indust. Microbiol., 13, 121–249, 1974 by E. O. Bennett, the entire contents of which are incorporated herein by reference. Over the years, samples of spoiled coolants have been obtained from many sources. These samples have been kept viable by growing them in metal working fluids. The inoculum employed in the antimicrobial tests contains these organisms and is aerated at all times. Normally, it contains between ten million to one hundred million organisms per ml.

Initially and once each week thereafter all units were inoculated with 1.0 ml of a 50—50 mixture of the two inocula (i.e., bacteria and fungi). The units were kept at ambient temperatures (27.0° C. to 28.5° C.).

The test units were studied for their microbiol content at weekly intervals by making serial dilutions of the coolant into a medium as described in the Prog. Indust. Microbial. article noted above. Each unit was studied for so long as the counts remained below 100,000 organisms/ml. Two consecutive counts in excess of this figure at weekly intervals was considered to constitute the point of "failure", and the test was discontinued at that time.

Since the test vessels were under constant aeration, there was considerable evaporation from each jar unit. The units were calibrated at the 600 ml mark and once or twice each week distilled water was added to bring the liquid level back to this mark. Distilled water was used in order to avoid a buildup of inorganic salts which would have taken place if tap water had been employed.

Base control tests in each instance revealed that the coolants employed without the addition of chelating agent and/or hydantoin product failed within one week due to the growth of microorganisms.

Examples A and B are comparative examples; Examples 1 through 4 are illustrative embodiments of this invention.

| Coolant | Manufactuer |
|---|---|
| Max Mix Coolant | Mack Co. |
| Shell Emulsion | Shell Oil Co. |
| Vantrol Emulsion | Van Straaten Chemical Co. |
| Sun Emulsion | Sun Oil Corp. |
| Monroe Emulsion | Monroe Chemical Corp. |
| Norton Emulsion | Norton Co. |
| Shamrock Emulsion | F.E. Anderson Oil & Chemical Corp. |
| DoAll Coolant | Do All Co. |
| Quaker Coolant | Quaker Chemical Corp. |
| Texaco Emulsion | Texaco Inc. |
| Irmco Emulsion | Internatinal Refining & Manufacturing Corp. |
| Polar Chip Coolant | Polar Chip Inc. |
| Shercool Coolant | Sherwin Williams Chemicals Inc. |
| Sanson Emulsion | Sanson & Sons, Inc. |
| Lusol Coolant | F.E. Anderson Oil & Chemical Corp. |
| Trim Coolant | Master Chemical Corp. |
| Cimcool 5 Star Coolant | Cincinnati Milacron Corp. |
| Union Emulsion | Union Oil Corp. |

The coolants were mixed with water in a ratio of 1 to 40 (coolant to water). The results are set forth in Table 1 below, wherein the time in days is recorded when the count in such test reached the level of 100,000, as described above.

Test failures in less than 60 days or less were considered likely to be unacceptable from the standpoint of potential industrial and commercial applications. Furthermore, from both a technical and statistical standpoint any data between about 0 to 21 days can not be regarded as significantly different.

TABLE 1

| Coolant | Column A DMDMH-55 1500 ppm | Column B DMDMH-55 3000 ppm | Column C DMDMH-55 4500 ppm |
|---|---|---|---|
| 1. Max Mix Coolant | 56 | 105* | — |
| 2. Shell Emulsion | 0 | 0 | 0 |
| 3. Vantrol Emulsion | <u>14</u> | 7 | 0 |
| 4. Sun Emulsion | 0 | 0 | 7 |
| 5. Monroe Emulsion | 0 | 21 | 14 |
| 6. Norton Emulsion | <u>7</u> | <u>28</u> | <u>28</u> |
| 7. Shamrock Emulsion | <u>28</u> | 105* | 105* |
| 8. DoAll Coolant | <u>14</u> | 7 | <u>42</u> |
| 9. Quaker Coolant | <u>21</u> | <u>21</u> | <u>21</u> |
| 10. Texaco Emulsion | <u>0</u> | 14 | 14 |
| 11. Irmco Emulsion | 0 | 0 | 0 |
| 12. Polar Chip Coolant | 14 | <u>35</u> | 7 |
| 13. Shercool Coolant | 0 | 21 | 7 |
| 14. Sanson Emulsion | 0 | 0 | 0 |
| 15. Lusol Coolant | 0 | 35 | — |
| 16. Trim Coolant | <u>14</u> | — | — |
| 17. Cimcool 5 Star Coolant | 7 | <u>35</u> | — |
| 18. Union Emulsion | 0 | — | — |

All testing at 1 to 40 oil to water ratio.
*Still inhibitory when taken off test. Underlined number indicates failure due to moulds.

EXAMPLE A

A series of sample jar units were prepared according to the procedure outlined above in order to ascertain the anti-microbial effect of 1,3-dimethylol-5,5-dimethyl hydantoin.

Samples tested were (A) 1500 ppm of 55% aqueous solution of 1,3-dimethylol-5,5-dimethylhydantoin (hereinafter sometimes referred to as "DMDMH-55");
(B) 3000 ppm DMDMH-55; and
(C) 4500 ppm DMDMH-55.

The samples were tested with the following commercially available coolants (i.e. metal working fluids):

EXAMPLE B

A series of sample jar units were prepared according to the procedure outlined above in order to ascertain the antimicrobial effect of EDTA - diNa and diethylenetriamine pentaacetic acid (pentasodium salt). Samples tested were (A) 1000 ppm EDTA - diNa;
(B) 1500 ppm EDTA - diNa; and
(C) 1000 ppm DTPA - Na$_5$ The samples were tested with the same commercially available coolants (i.e., metal working fluids) used in Example 1.

The coolants were mixed with water in a ratio of 1 to 40 (coolant to water). The results are set forth in Table 2 below, wherein the time in days is recorded when the count in such test reached the level of 100,000, as described above.

TABLE 2

| | Coolant | Column A EDTA (1000 ppm) | Column B EDTA (1500 ppm) | Column C DTPA (1000 ppm) |
|---|---|---|---|---|
| 1. | Max Mix Coolant | 0 | — | — |
| 2. | Shell Emulsion | 7 | — | 105* |
| 3. | Vantrol Emulsion | 0 | 0 | 0 |
| 4. | Sun Emulsion | 0 | 0 | 0 |
| 5. | Monroe Emulsion | 35 | 35 | 105* |
| 6. | Norton Emulsion | 14 | 14 | <u>21</u> |
| 7. | Shamrock Emulsion | 7 | 7 | 0 |
| 8. | DoAll Coolant | 0 | 0 | 35 |
| 9. | Quaker Coolant | 7 | 0 | — |
| 10. | Texaco Emulsion | 7 | — | — |
| 11. | Irmco Emulsion | 0 | — | — |
| 12. | Polar Chip Coolant | 0 | 0 | — |
| 13. | Shercool Coolant | 7 | 7 | — |
| 14. | Sanson Emulsion | — | 7 | — |
| 15. | Lusol Coolant | — | 0 | — |
| 16. | Trim Coolant | — | 0 | — |
| 17. | Cimcool 5 Star Coolant | — | 7 | — |
| 18. | Union Emulsion | — | 0 | — |

All testing at 1 to 40 oil to water ratio.
*Still inhibitory when taken off test.
Underlined number indicates failure due to moulds.

EXAMPLE 1

A series of sample jar units were prepared according to the procedure outlined above in order to ascertain the antimicrobial effect of EDTA - diNa and 1,3-dimethylol-5,5-dimethyl hydantoin. Samples tested were (A) 1500 ppm EDTA - diNa;
(B) 1500 ppm of 55% aqueous solution of 1,3-dimethylol-5,5-dimethylhydantoin (hereinafter sometimes referred to as "DMDMH-55"); and
(C) 1500 ppm EDTA - diNa and 1500 ppm DMDMH-55.

The samples were tested with commercially available coolants (i.e., metal working fluids).

The coolants were mixed with water in a ratio of 1 to 40 (coolant to water). The results are set forth in Table 3 below, wherein the time in days is recorded when the count in such test reached the level of 100,000, as described above.

EXAMPLE 2

A series of sample jar units were prepared according to the procedure outlined above in order to ascertain the antimicrobial effect of EDTA - diNa or tetra Na and 1,3-dimethylol-5,5-dimethylhydantoin. Samples tested were (A) 500 ppm EDTA - diNa and 2500 ppm DMDMH-55; and
(B) 500 ppm EDTA - tetra Na and 2500 ppm DMDMH-55.

The samples were tested with the following commercially available coolants (i.e., metal working fluids):

Coolant

Monroe Emulsion
Norton Emulsion
DoAll Coolant
Quaker Coolant
Polar Chip Coolant
Shercool Coolant The coolants were mixed with water in a ratio of 1 to 40 (coolant to water) as above. In each instance, after a

TABLE 3

| | | Column A EDTA (1500 ppm) | Column B DMDMH-55 1500 ppm | Column C 1500 ppm DMDMH-55 1500 ppm EDTA |
|---|---|---|---|---|
| 1. | Vantrol Emulsion | 0 | <u>14</u> | 84 |
| 2. | Sun Emulsion | 0 | 0 | 105* |
| 3. | Monroe Emulsion | 35 | 0 | 35 |
| 4. | Norton Emulsion | 14 | <u>7</u> | 105* |
| 5. | Shamrock Emulsion | 7 | <u>28</u> | 105* |
| 6. | DoAll Coolant | 0 | <u>14</u> | 105* |
| 7. | Quaker Coolant | 0 | <u>21</u> | 105* |
| 8. | Polar Chip Coolant | 0 | 14 | 105* |
| 9. | Shercool Coolant | 7 | 0 | 105* |
| 10. | Sanson Emulsion | 7 | 0 | 105* |
| 11. | Lusol Coolant | 0 | 0 | 105* |
| 12. | Trim Coolant | 0 | 14 | 105* |
| 13. | Cimcool 5 Star Coolant | 7 | 7 | 105* |
| 14. | Union Emulsion | 0 | 0 | 49 |

All testing at 1 to 40 oil to water ratio.
*Still inhibitory when taken off test.
Underlined number incidates failure due to moulds.

period of 105 days the units were still inhibited from the growth of bacteria and fungi.

EXAMPLE 3

A series of sample jar units were prepared in the same manner as Examples 1-4 in order to determine the antimicrobial effect of diethylenetriamine pentaacetic acid (pentasodium salt) and DMDMH-55. Samples tested contained 2500 ppm DMDMH-55 and 500 ppm DTPA $Na_5$.

The samples were tested with the following coolants:
DoAll;
Shercool;
Polar Chip;
Quaker;
Norton Emulsion; and
Monroe Emulsion.

The coolants were mixed with water in a ratio of 1 to 40 (coolant to water). The results are set forth in Table 4 below, wherein the time in days is recorded when the count in such test reached the level of 100,000, as described above.

TABLE 4

| Coolant | 2500 DMDMH-55 500 DTPA $Na_5$ |
|---|---|
| DoAll Coolant | 105* |
| Shercool Coolant | 84 |
| Polar Chip Coolant | 105* |
| Quaker Coolent | 105* |
| Norton Emulsion | 105* |
| Monroe Emulsion | 105* |

*Still inhibitory when taken off test

EXAMPLE 4

A series of sample jar units were prepared according to the procedure above in order to ascertain the antimicrobial effect of 500 ppm EDTA-diNa and 1500 ppm DMDMH-55. The samples were tested in the same manner and with the same coolants used in Example 3. The results are set forth in Table 5 below.

TABLE 5

| Coolant | 1500 DMDMH-55 500 EDTA $Na_2$ |
|---|---|
| DoAll Coolant | 63 |
| Shercool Coolant | 105* |
| Polar Chip Coolant | 105* |
| Quaker Coolant | 105* |
| Norton Emulsion | 35 |
| Monroe Emulsion | 105* |

Notes:
1. Numbers designate days inhibition.
2. Underlined numbers, indicates test failure due to mold.
3. *Still inhibitory when taken off test.

It will be noted that when EDTA is used in combination with DMDMH, the test results show that generally the resulting antimicrobial control was maintained for multifold periods of time longer than was observed for the same amount of either EDTA or DMDMH used alone (at equivalent concentrations).

The antimicrobial composition formulations of the present invention are particularly attractive due to the low toxicity of their components when present in the amounts indicated. Furthermore, while prior known antimicrobial formulations appear to be effective at best in only about 42% of the commercially available metal working fluids, the formulations of the present invention are more universally effective.

While the invention has been explained in relation to certain illustrative embodiments of it, it is understood that many modifications and substitutions may be made in any of the specific embodiments within the scope of the appended claims which are intended also to cover equivalents of them. Furthermore, the invention may comprise, consist or consist essentially of the herein recited steps and materials.

We claim:

1. An antimicrobial composition formulation for combating bacteria and fungi comprising as active ingredients an admixture of a condensation product of 5,5-dimethyl hydantoin and formaldehyde with a water-soluble chelating agent selected from the group consisting of the alkali metal salts of ethylenedediaminetetraacetic acid and diethylenetriaminepentaacetic acid said condensation product being formed by the condensation of 1,2 or more moles of formaldehyde with each mole of 5,5-dimethylhydantoin, the ratio by weight of said condensation product to said chelating agent ranging from 0-25:1 to 20:1, whereby said chelating agent potentiates the anti-microbial activity of said formulation.

2. An antimicrobial composition formulation according to claim 1 wherein such condensation product is selected from the group consisting of 1,3-dimethylol-5,5-dimethyl hydantoin; 1-mono-methylol-5,5-dimethyl hydantoin and 3-mono-methylol-5,5-dimethyl hydantoin.

3. An antimicrobial composition formulation according to claim 1 comprising as active ingredients an admixture of (1,3-dimethylol-5,5-dimethylhydantoin) and a water soluble salt of ethylenediaminetetraacetic acid.

4. An antimicrobial composition formulation according to claim 1 in the form of an aqueous solution.

5. An antimicrobial composition formulation according to claim 1 comprising 1,3-dimethylol-5,5-dimethyl-hydantoin and the disodium or tetrasodium salt of ethylenediaminetetraacetic acid.

6. An antimicrobial composition formulation according to claim 1 comprising 1,3-dimethylol-5,5-dimethyl-hydantoin and the disodium salt of ethylenediaminetetraacetic acid.

7. A method of inhibiting the growth of bacteria and fungi in an aqueous fluid medium susceptible to such growth which comprises adding to said medium an inhibitive amount of the composition formulation of claim 1.

8. A method according to claim 7 wherein there is added to said medium by weight at least 500 parts of a water-soluble salt of ethylenediaminetetraacetic acid per million parts of said medium and at least 500 parts of 1,3-dimethylol-5,5-dimethylhydantoin.

9. A method according to claim 7 wherein there is added to said medium by weight:
(a) about 500 to 10,000 parts of 1,3-dimethylol-5,5-dimethylhydantoin; and
(b) about 500 to 4000 parts of a water-soluble salt of ethylenediaminetetraacetic acid,
said parts based on one million parts of said medium.

10. A method according to claim 9 wherein the ratio by weight of 1,3-dimethylol-5,5-dimethylhydantoin to water-soluble salt of ethylenediaminetetraacetic acid ranges from 0.25:1 to 20:1.

* * * * *

UNITED STATES PATENT AND TRADEMARK OFFICE
CERTIFICATE OF CORRECTION

PATENT NO. : 4,172,140

DATED : October 23, 1979

INVENTOR(S) : Shull, Samuel Ellsworth; Bennett, Edward O.

It is certified that error appears in the above-identified patent and that said Letters Patent is hereby corrected as shown below:

COLUMN 10

Claim 1, line 3 from the bottom substitute
"from 0.25:1 to 20:1" for--from 0-25:1 to
20:1--

Signed and Sealed this

Sixteenth Day of April 1985

[SEAL]

Attest:

DONALD J. QUIGG

Attesting Officer  Acting Commissioner of Patents and Trademarks